US010500233B2

(12) United States Patent
Hoffmann et al.

(10) Patent No.: US 10,500,233 B2
(45) Date of Patent: *Dec. 10, 2019

(54) COMPOSITIONS AND METHODS FOR TREATING BONE, JOINTS AND CARTILAGE

(71) Applicant: REPLICEL LIFE SCIENCES INC., Vancouver (CA)

(72) Inventors: Rolf Hoffmann, Freiburg (DE); Kevin John McElwee, Vancouver (CA)

(73) Assignee: RepliCel Life Sciences Inc., Vancouver (CA)

(*) Notice: Subject to any disclaimer, the term of this patent is extended or adjusted under 35 U.S.C. 154(b) by 102 days.

This patent is subject to a terminal disclaimer.

(21) Appl. No.: 15/118,391

(22) PCT Filed: Feb. 12, 2015

(86) PCT No.: PCT/US2015/015721
§ 371 (c)(1),
(2) Date: Aug. 11, 2016

(87) PCT Pub. No.: WO2015/123477
PCT Pub. Date: Aug. 20, 2015

(65) Prior Publication Data
US 2017/0173084 A1    Jun. 22, 2017

Related U.S. Application Data

(60) Provisional application No. 61/939,187, filed on Feb. 12, 2014.

(51) Int. Cl.
| *A61K 35/36* | (2015.01) |
| *A61K 35/16* | (2015.01) |
| *C12N 5/00* | (2006.01) |
| *A61K 38/18* | (2006.01) |
| *A61K 38/39* | (2006.01) |
| *A61K 31/728* | (2006.01) |
| *A61K 45/06* | (2006.01) |
| *C12N 5/071* | (2010.01) |

(52) U.S. Cl.
CPC ............ *A61K 35/36* (2013.01); *A61K 31/728* (2013.01); *A61K 35/16* (2013.01); *A61K 38/18* (2013.01); *A61K 38/39* (2013.01); *A61K 45/06* (2013.01); *C12N 5/0627* (2013.01)

(58) Field of Classification Search
CPC ........ C12N 5/00; C12N 5/0627; A61K 35/36; A61K 35/16; A61K 38/18; A61K 38/39
See application file for complete search history.

(56) References Cited

U.S. PATENT DOCUMENTS

| 5,556,783 | A | 9/1996 | Lavker et al. |
| 5,736,372 | A | 4/1998 | Vacanti et al. |
| 5,750,657 | A | 5/1998 | Edwardson et al. |
| 5,759,830 | A | 6/1998 | Vacanti et al. |
| 6,607,745 | B2 | 8/2003 | Leneau |
| 7,556,825 | B2 | 7/2009 | Li et al. |
| 7,875,296 | B2 | 1/2011 | Binette |
| 8,039,021 | B2 | 10/2011 | Royer |
| 8,039,258 | B2 | 10/2011 | Harris et al. |
| 8,105,380 | B2 | 1/2012 | Kharazi et al. |
| 8,343,520 | B2 | 1/2013 | Seigneurin et al. |
| 8,349,338 | B2 | 1/2013 | Loginova et al. |
| 8,431,400 | B2* | 4/2013 | Hoffmann ............ C12N 5/0628 435/325 |
| 2002/0005205 | A1* | 1/2002 | Barry ................... C12N 5/0663 128/898 |
| 2002/0172705 | A1 | 11/2002 | Murphy et al. |
| 2004/0057937 | A1 | 3/2004 | Jahoda et al. |
| 2005/0239897 | A1 | 10/2005 | Pittenger |
| 2006/0088505 | A1 | 4/2006 | Hoffmann |
| 2008/0118478 | A1 | 5/2008 | Kleinsek |
| 2008/0284763 | A1 | 11/2008 | Someya et al. |
| 2009/0130068 | A1 | 5/2009 | Eklund |
| 2009/0142836 | A1 | 6/2009 | Wang et al. |
| 2010/0047305 | A1 | 2/2010 | Naughton et al. |
| 2010/0124573 | A1 | 5/2010 | Naughton et al. |
| 2010/0197019 | A1 | 8/2010 | Toyoshima et al. |

(Continued)

FOREIGN PATENT DOCUMENTS

| DE | 10056465 | 7/2002 |
| EP | 0980270 | 12/2003 |

(Continued)

OTHER PUBLICATIONS

International Search Report and Written Opinion dated Oct. 4, 2014 for Application No. PCT/US2014/016109.
International Search Report and Written Opinion dated Sep. 17, 2014 for Application No. PCT/US2014/043048.
International Search Report and Written Opinion dated May 18, 2015 for Application No. PCT/US2015/015720.
International Search Report and Written Opinion dated May 14, 2015 for Application No. PCT/US2015/015721.
European Supplemental Search Report dated Oct. 11, 2016 for Application No. 14706762.3.
Bajpai, Vivek K. et al., "Clonal multipotency and effect of long-term in vitro expansion on differentiation potential of human hair follicle derived mesenchymal stem cells", Stem Cell Research, 2012, vol. 8, pp. 74-84.

(Continued)

*Primary Examiner* — Ruth A Davis
(74) *Attorney, Agent, or Firm* — BioMed IP

(57) ABSTRACT

Briefly stated, the present invention provides compositions and methods for treating or preventing joint injuries utilizing hair follicle derived Non-Bulbar Dermal Sheath ("NDBS") cells. Within one aspect of the invention methods are provided for isolating NBDS cells, comprising the steps of: (a) preparing vital hair; (b) cleaving the hair prepared in step (a) to remove the hair follicle bulb; (c) isolating Non-Bulbar Dermal Sheath tissue; and (d) cultivating the isolated Non-Bulbar Dermal sheath tissue to produce NBDS cells. Within one embodiment of the invention the vital hair is obtained by full skin biopsy from the occipital scalp of a subject.

20 Claims, 2 Drawing Sheets

(56) References Cited

U.S. PATENT DOCUMENTS

| | | |
|---|---|---|
| 2010/0247494 A1 | 9/2010 | Gregory et al. |
| 2010/0273231 A1 | 10/2010 | Andreadis |
| 2010/0323027 A1 | 12/2010 | Lim |
| 2011/0185439 A1 | 7/2011 | Gaitanaris et al. |
| 2011/0293667 A1 | 12/2011 | Baksh et al. |
| 2012/0192296 A1 | 7/2012 | Schneider et al. |
| 2015/0374757 A1 | 12/2015 | Hoffmann et al. |
| 2016/0136206 A1 | 5/2016 | Hoffmann et al. |
| 2017/0165299 A1 | 6/2017 | Hoffmann et al. |
| 2017/0173084 A1 | 6/2017 | Hoffmann et al. |

FOREIGN PATENT DOCUMENTS

| | | |
|---|---|---|
| EP | 1226234 | 6/2011 |
| WO | 1995001423 | 1/1995 |
| WO | 2003104443 | 12/2003 |
| WO | 2012078649 | 6/2012 |
| WO | 2013113121 | 8/2013 |
| WO | 2014127047 | 8/2014 |
| WO | 2014205142 | 12/2014 |
| WO | 2015123476 | 8/2015 |
| WO | 2015123477 | 8/2015 |

OTHER PUBLICATIONS

Beckman, Brett, "Potential help for refractory feline chronic gingivo-stomatitis (proceedings)", dvm360, http://veterinarycalendar.dvm360.com/potential-help-refractory-feline-chronic-gingivo-stomatitis-proceedings, Oct. 1, 2008, pp. 1-3.

Eicheler, Wolfgang et al., "5[alpha]-reductase activity in the human hair follicle conentrates in the dermal papilla", Archives of Dermatological Research, vol. 290, No. 3, Mar. 1, 1998, pp. 126-132.

Gasnereau et al., "Flow cytometry to sort mammalian cells in cytokinesis", Cytometry Part A, 71A, 2007, pp. 1-7.

Hoogduijn et al., "Comparative characterization of hair follicle dermal stem cells and bone marrow mesenchymal stem cells", Stem Cells and Development, 2006, vol. 15, pp. 49-60.

Imai, Ryusuke et al., "Organ culture conditions of human hair follicles", Journal of Dermatological Science, vol. 3, 1992, pp. 163-171.

Jahoda, C A B et al., "Hair follicle dermal cells differentiate into adipogenic and osteogenic lineages", Experimental Dermatology Blackwell Munsgaard, Copenhagen, DK, vol. 12, No. 6, Dec. 1, 2003, pp. 849-859.

Jindo, Toshimasa et al, "The effect of hepatocyte growth factor/scatter factor on human hair follicle growth", Journal of Dermatological Science, vol. 10, 1995, pp. 229-232.

Journal of Dermatological Science, Letter to the Editor, "Connective tissue sheath of hair follicle is a major source of dermal type 1 procollagen in human scalp", vol. 68, 2012, pp. 194-204.

Liu, Jin Yu et al., "Derivation of functional smooth muscle cells from multipotent human hair follicle mesenchymal stem cells", Tissue Engineering Part A, vol. 16, No. 8, Aug. 1, 2010, pp. 2553-3341.

Liu, Jin Yu et al., "Contractile smooth muscle cells derived from hair-follicle stem cells", Cardiovascular Research, vol. 79, 2008, pp. 24-33.

McElwee, Kevin J et al., "Macrophage-Stimulating protein promotes hair growth ex vivo and induces anagen from telogen stage hair follicle in vivo", The Journal of Investigative Dermatology, 2004, vol. 123, pp. 34-40.

McElwee, K J et al., "Cultured peribulber dermal sheath cells can induce hair follicle development and contribute to the dermal sheath and dermal papilla", The Journal of Investigative Dermatology, Nature Publishing Group, GB, vol. 121, Jan. 1, 2003, pp. 1267-1275.

Wu et al., "Enzyme Digestion to Isolate and Culture Human Scalp Dermal Papilla Cells: a More Efficient Method", Arch Dermatol. Res. 297, 2005, pp. 60-67.

Young, R G et al., "Use of mesenchymal stem cells in a collagen matrix for achilles tendon repair", Journal of Orthopaedic Research, vol. 16, No. 4, Jul. 1, 1998, pp. 406-413.

\* cited by examiner

COMPOSITIONS AND METHODS FOR TREATING BONE, JOINTS AND CARTILAGE

CROSS-REFERENCE TO RELATED APPLICATION

This application is a national phase application under 35 U.S.C. § 371 of International Application No. PCT/US2015/015721, filed Feb. 12, 2015, which claims the benefit under 35 U.S.C. § 119(e) of U.S. Provisional Patent Application No. 61/939,187 filed Feb. 12, 2014, which applications are incorporated herein by reference in their entirety.

FIELD OF THE INVENTION

The present invention relates to compositions and methods for treating joints and adjacent bone or cartilage as well for various medical purposes, and more specifically, to compositions comprising of autologous or allogenic non-bulbar dermal sheath (NDBS) cells for use in the treatment and repair of joints, including for example, joint injuries and of osteoarthritis, as well as for various other medical purposes

BACKGROUND

Description of the Related Art

A joint is a body part at which bones (two or more) interconnect. Joints are designed to allow movements and mechanical support. They are classified by their structure and function.

The structural classification describes how bones connect to each other, whereas the functional classification describes the degree of movement between the connecting bones. There is considerable overlap in the classifications.

A joint injury is defined as an arthropathy, and with additional inflammation of at least one joint the disorder is then called arthritis. Most joint injuries involve arthritis.

Osteoarthritis (OA), which is also known as degenerative arthritis, degenerative joint disease or osteoarthritis, is a group of some mechanical abnormalities including the degradation of joints, the articular cartilage and also subchondral bone. Osteoarthritis is the most common form of arthritis worldwide, and is the leading cause of chronic disability in many countries such as the United States where it affects nearly 27 million people. Typical clinical symptoms may include pain of joints, tenderness, stiffness, and sometimes effusion of joints. The diagnosis can be made based on history and clinical examination. X-rays confirm the diagnosis but are not mandatory. Usually other imaging techniques such as ultrasound or MRI are not necessary but sometimes done to clinically diagnose osteoarthritis or the underlying causes. Arthroscopy is sometimes performed.

Osteoarthritis can be classified into either primary or secondary, which largely depends on whether or not there is an underlying cause.

Primary osteoarthritis is a chronic degenerative disorder, which is related to aging. With aging the cartilage water content decreases, as a result of a reduced proteoglycan amount. In healthy cartilage the water content is finely balanced where collagen fibers exert the compressive force. During onset of osteoarthritis the amount of fluid in the cartilage increases, and furthermore there is a loss of collagen. Thereby the collagen fibers become susceptible to degradation and degenerate. Breakdown products are released into the synovial space, and inflammation will follow. This cascade of events is followed by destruction of cartilage and subchondral bone and by new bone outgrowth or osteophytes, which then eventually ends up in osteoarthritis.

Secondary osteoarthritis can be due to different damages from mechanical stress and subsequent improper healing by the joints. The sources of this stress are manifold and may include: malalignments of bones caused by congenital or pathogenic causes; mechanical injury such as incurred by accidents or surgery; excess or high body weight and thereby immobility of joints leading to weak muscles which cannot support the joints. The impairment of peripheral nerves by trauma or metabolic diseases which lead to sudden or uncoordinated movements.

It is a general belief that there is a hereditary background to osteoarthritis as a number of studies have shown that there is a greater prevalence of the disease among siblings. In general post-menopausal women are more likely to develop osteoarthritis, compared to age-matched males. Other secondary types of osteoarthritis are secondary and caused by other factors, but the resulting pathology is the same as for primary osteoarthritis. As examples, those diseases might be metabolical diseases such as alkaptonuria, diabetes, hemochromatosis, gout or congenital disorders such as Marfan syndrome, or septic arthritis, or other inflammatory diseases such as Perthes' disease, Lyme disease and all other forms of chronic arthritis (e.g. rheumatoid arthritis). Also injuries to adjacent ligaments and menisci, as a result of accidents or surgeries may end up in osteoarthritis where ligamentous deterioration or instability is the triggering factor. As a consequence of those causes, a process is initiated leading to loss of cartilage. Later on the bone surfaces become less well protected by cartilage, bone is then exposed and damaged. This results in decreased movement secondary to pain, regional muscles atrophy, and lax ligaments develop.

Osteoarthritis typically affects the hands, feet, spine, and the large weight bearing joints such as the hips, but any joint can be affected. When osteoarthritis progresses, the affected joints get larger and stiffer and more painful. With gentle use they feel better, but worse with excessive or prolonged use. At the fingers, so called Heberden's nodes may develop.

Treatment is generally multimodal and involves a combination of a change in lifestyle, exercise (weight loss, physiotherapy, moderate exercise) and analgesics. Joint replacement surgery may be needed at some point in time. Paracetamol is the first line therapy and NSAIDs as add on therapy. Injection of glucocorticoids (such as hydrocortisone and others) delivers only short term pain relief, but are associated with harmful side effects such as infections, as well as injections of hyaluronic acid.

While there are a number of surgical and non-surgical methods that can be used to treat osteoarthritis or other joint injuries, none of these techniques addresses the issue of a cellular deficit of functional, collagen-producing and immunoregulative fibroblasts in the injured joint.

The present invention discloses novel compositions and methods for treating joint injuries, and further provides other related advantages.

SUMMARY

Briefly stated, the present invention provides compositions and methods for treating or preventing joint injuries utilizing hair follicle derived Non-Bulbar Dermal Sheath ("NDBS") cells. Within one aspect of the invention methods are provided for isolating NBDS cells, comprising the steps of: (a) preparing vital hair; (b) cleaving the hair prepared in step (a) to remove the hair follicle bulb (which contains the dermal sheath cup and dermal papilla); (c) isolating Non-Bulbar Dermal Sheath tissue; and (d) cultivating the isolated Non-Bulbar Dermal sheath tissue to produce NBDS cells. The use of NBDS cells can either be autologous or allogenic. Within one embodiment of the invention the vital hair is obtained by full skin biopsy from the occipital scalp of a subject. Within another embodiment the hair is cleaved utilizing a micromanipulator such as a needle along with a scalpel or pair of scissors. Within yet other embodiments, the methods provided herein further comprise the step of conducting enzymatic digestion of the isolated Non-Bulbar Dermal Sheath tissue, optionally with, for example, collagen digesting enzymes such as collagenase, hyaluronidase, DNAse, elastase, papain, protease type XIV, trypsin, dispase, and leupeptin. Within further embodiments, the cells are passaged over multiple passages.

Within other aspects of the invention, isolated NBDS cells are provided, optionally prepared according to the methods described above. These NBDS cells may be contained within compositions with a variety of ingredients, such as, for example, blood plasma, blood serum, albumin (e.g., human albumin), platelet-rich plasma (PRP), fibrin, and/or hyaluronic acid. Other ingredients may also be included within these compositions, including for example, components of the extracellular matrix (e.g., glycosaminoglycans (GAGs), heparin sulfate, chondroitin sulfate, keratin sulfate, hyaluronic acid, elastin, fibronectins, fibrin, composite scaffolds, collagens and laminins, or any other soluble or insoluble extracellular matrix), cytokines and chemokines (e.g., transforming growth factor beta (TGF-beta) and its isoforms, insulin-like growth factor (IGF) and its isoforms, granulocyte-macrophage colony-stimulating factor (GM-CSF), parathyroid-hormone-related protein, hepatocyte growth factor/scatter factor (HGF/SF), macrophage stimulating protein (MSP), epidermal growth factor (EGF), interleukin 6 (IL-6), stromal cell-derived factor 1 (SDF-1), platelet derived growth factor (PDGF) and fibroblast growth factor (FGF) and/or various therapeutic agents (e.g., analgesic agents, anti-inflammatory agents antibiotics, antimycotics and immunomodulatory agents).

Within yet other aspects of the invention methods are provided for treating the joint of a subject, comprising the step of administering to the joint of a subject a composition comprising NBDS cells as described herein. Within one embodiment, the subject is a mammal selected from the group consisting of humans, horses, dogs and cats. Within various embodiments the treatment is due to a joint injury. Within certain embodiments, the joint injury results in osteoarthritis, which can be either primary or secondary. Within yet another embodiment, the joint can be every joint on the entire human body, or a selected joint of the body (such as the hands or toes).

The details of one or more embodiments are set forth in the description below. Other features, objects and advantages will be apparent from the description, the drawings, and the claims. In addition, the disclosures of all patents and patent applications referenced herein are incorporated by reference in their entirety.

BRIEF DESCRIPTION OF THE DRAWINGS

FIG. 1 illustrates the dissection of a human hair follicle.

DETAILED DESCRIPTION OF THE INVENTION

As noted above, the present invention provides hair follicle derived Non-Bulbar Dermal Sheath (NDBS) cells for use in the treatment or prevention of joint aging and joint injuries within a mammal, which eventually give way to osteoarthritis. Prior to setting forth the invention however, it may be helpful to an understanding thereof to first set forth definitions of certain terms that are used hereinafter.

Non-Bulbar Dermal Sheath cells, or "NBDS" cells, refers to dermally derived cells (or more specifically, derived from hair follicles). Within preferred embodiments, the sheath cells are obtained from the outer dermal sheath of a hair follicle, above the bulbar portion of the hair root (i.e., above the dermal papilla and dermal sheath cup cells), but below the base of the sebaceous gland canal. NBDS cells may be readily identified by a number of methods, including for example, by the method of preparation and culture (as described below); morphology (see, e.g., FIG. 2); as well as cell specific markers (e.g., NBDS cells are primarily positive for CD 90, CD73 and CD49b, and/or primarily negative for CD34, CD45 and KRT14, either before or after culturing). In all events however, the cells must be of a dermal origin, and more specifically, of a follicular origin.

Expanded Non-Bulbar Dermal Sheath cells, or "eNBDS cells" refers to NBDS cells which have been expanded for several passages in culture, but which retain the ability to produce collagen (e.g., type I collagen) as well as a variety of cytokines and chemokines. As above, unexpectedly, the eNBDS cells can also be immunoregulatory. Within preferred embodiments, the cells can be expanded in culture for 1, 2, 3, 4, 5, 10, 20 or more passages.

"Isolated" NBDS cells refers to a cell population of greater than 70%, 80%, 85%, 90%, 95%, 98%, or 100% NBDS cells. NBDS cells have the ability to produce collagen (e.g., type I collagen), as well as a variety of cytokines and chemokines. Unexpectedly, the NBDS cells can also be immunoregulatory, making them particularly suitable for treatment of tendon injuries (e.g., by assisting in suppressing any inflammatory response).

Figure 2:
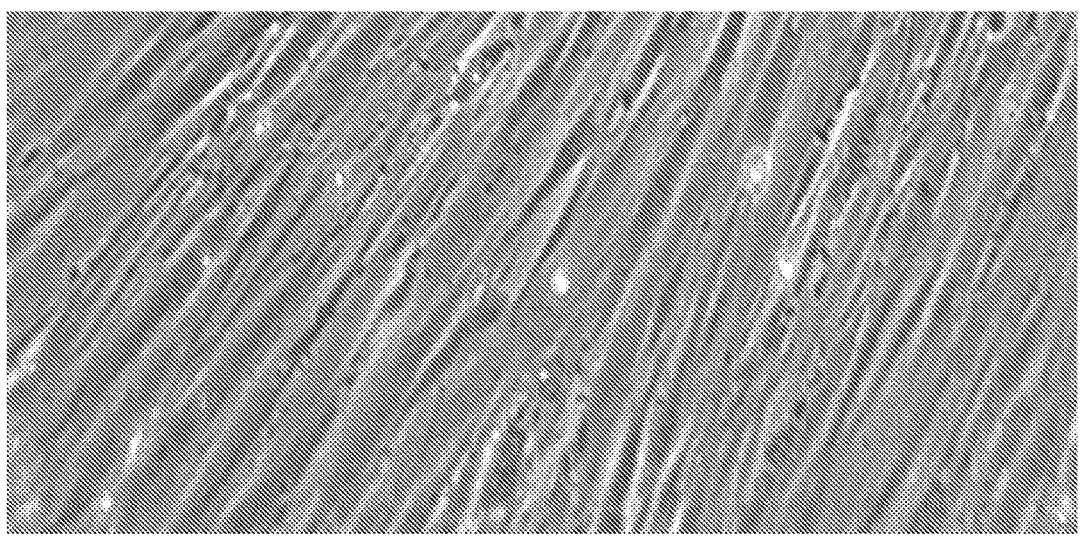
FIG. 2 is a photomicrograph of NBDS cells in culture.

Within certain embodiments of the invention, software or other visualization techniques that can be utilized to visualize cells on a microscopic scale can be used to assess the size, shape, viability and granularity of a large number of cells in a visual field, and ascertain the number of NBDS cells (which are fibroblast-like as shown in FIG. 2), as opposed to keratinocytes, melanocytes DSCs, and other cell types which are of different morphology). Hence, within one embodiment of the invention methods are provided for isolating NBDS cells comprising the step of culturing cells over at least 1, 2, 3, 4, 5, 6, 10, or 20 passages from a hair follicle such that an isolated population of NBDS cells is produced. Within preferred embodiments the cells placed into dishes or flasks which allow the NBDS cells to adhere, and with each passage non-adherent cells are removed, and the remaining adherent cells released (e.g., by trypsinization), followed by addition of fresh media. Within such embodiments it can be determined when a sufficient population of isolated NBDS cells has been obtained by visualizing the cells in the cell culture in order to assess the number of NBDS cells vs. non-NBDS cells. Visualization techniques include, but are not limited to direct microscopic visualization, staining of the cells for markers (or lack thereof—e.g., for lack of keratin), and light/laser analysis to look at diffraction patterns of the different cell types (see, generally "Laser Scanning Microscopy and Quantitative Image Analysis of Neuronal Tissue" Lidia Bakota and Roland Brandt, eds., Humana Press, 2014; see also "Imaging and Spectroscopic Analysis of Living Cells: Optical and Spectroscopic Techniques", Conn ed., Academic Press, 2012)

Within other embodiments, cell specific markers (e.g., NBDS cells are primarily positive for CD 90, CD73 and CD49b, and/or primarily negative for CD34, CD45 and KRT14 (optionally before or after culturing) can be utilized to assess the degree of NBDS cells vs. contaminant cell types. "Applications of Flow Cytometry in Stem Cell Research and Tissue Regeneration", Krishan, Krishnamurthy, and Totey eds., Wiley-Blackwell, 2010). For example, isolated NBDS cells may be prepared by a) obtaining one or more vital hair follicles; b) releasing cells from the hair follicle (e.g., through the use of enzymes, or by culturing growing cells out of the hair follicle); and c) sorting the cells (e.g., by flow cytometry or through the use of magnetic beads) to obtain a population of isolated NBDS cells. Within certain embodiments of the invention cells in any stage of the process may be optionally cultured as described above (e.g., cells may be cultured for at least 1, 2, 3, 4, 5, 6, 10 or 20 passages as described above, and the resultant cells further isolated by, for example, flow cytometry or magnetic beads.

Within preferred embodiments the isolated NBDS cells are at least 70%, 80%, 85%, 90%,95%, 98%, or 100% positive for one or more of the positive markers described above, and/or at least 80%, 90%, 95%, or 98% negative for one of the negative markers described above.

Within preferred embodiments of the invention (and utilizing any of the techniques described herein), isolated NBDS cells have less than 15%, 10%, 5%, or 1% keratinocytes within the cell population and/or less than 15%, 10%, 5%, or 1% melanocytes within the cell population. However, within further embodiments, the isolated NBDS cell population is derived from a population of dermal cells (preferably, from hair follicles) that have some contaminating cell types, including for example, at least 1, 5, 10, 0.0.01%, 0.1%, or 1% keratinocytes in the cell population, and/or at least 5, 10, 0.1%, 0.1% melanocytes. Within further embodiments of the invention the isolated NBDS cells are at least 95% pure, and have at least one contaminating cell type (e.g., at least one keratinocyte) within the cell population.

"Joint injuries" refers to damage of the joints due to external or internal trauma or genetic predisposition. These injuries eventually lead to osteoarthritis. These injuries can be primary or secondary in nature.

Preparation of NBDS

As noted above, the present invention provides methods for isolating NBDS cells. Within one aspect of the invention, such methods comprise the steps of (a) preparing vital hair; (b) cleaving the hair prepared in step (a) to remove the hair follicle bulb (which contains the dermal sheath cup and dermal papilla); (c) isolating Non-Bulbar Dermal Sheath tissue; and (d) cultivating the isolated Non-Bulbar Dermal sheath tissue to produce NBDS cells.

In order to prepare vital (or 'living') hair, a sample is typically obtained from a given subject (e.g., a mammal such as a human, horse, cat or dog). The sample may be obtained from a variety of sites (e.g., for humans, from the occipital area of the scalp, the chest or thigh, and for horses from the mane or tail). The sample may be obtained via a biopsy, or other suitable means (e.g., by 'plucking', or dissection, or micro-dissection, enzymatic digestion, enzyme digestion-assisted dissection). Preferably, hair follicles in the anagen phase of development are selected, although other phases of development (e.g., the catagen phase and telogen phase) can also be utilized.

Figures 1A, 1B, 1C, 1D:
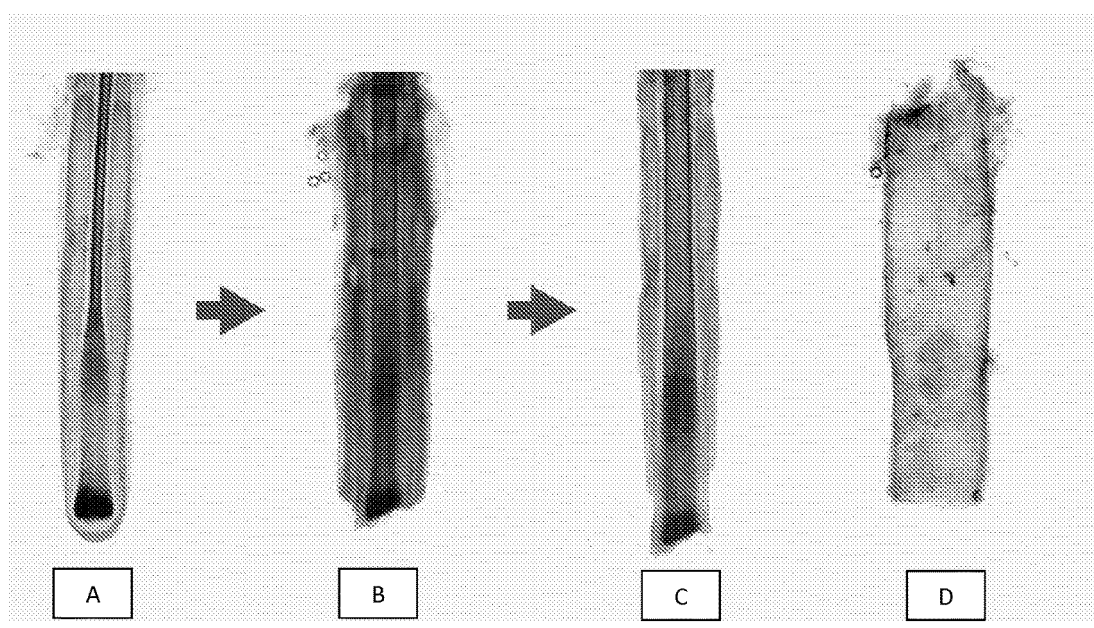
FIG. 1A shows an isolated human hair follicle, which can be cleaved above the bulbar portion of the hair root (i.e., above the dermal papilla and dermal sheath cup cells, i.e., above the end bulbs), but below the base of the sebaceous gland canal, in order to obtain an isolated dermal sheath (see FIG. 1B). The structure depicted in FIG. 1B can be separated into at least two separate components, as shown in FIGS. 1C and 1D.
FIG. 1C depicts the hair fiber and associated inner root sheath, and outer root sheath which contain predominantly keratinocytes.
FIG. 1D is the dermal sheath containing NBDS cells (also occasionally referred to as the connective-tissue sheath, upper dermal sheath or less precisely just dermal sheath). In contrast to other types of cells, NBDS cells are highly positive for a collagen-1 marker and only weakly positive for alkaline phosphatase and steroidsulfatase. In addition, these cells express markers such as CD90 and other stem cell markers.

Once the sample is obtained from the subject, the sample is then separated to isolate the hair follicle, typically utilizing a micromanipulator such as a needle, and a scalpel or pair of scissors, although other instruments such as needles, scissors may also be utilized. Within certain embodiments, the isolated hair follicle as shown in FIG. 1A can be further cleaved above the bulbar portion of the hair root (i.e., above the dermal papilla and dermal sheath cup cells), but below the base of the sebaceous gland canal in order to obtain an isolated upper dermal sheath (see FIG. 1B). The structure depicted in FIG. 1B can be separated into at least two separate components, as shown in FIGS. 1C and 1D. FIG. 1C depicts the hair fiber and associated inner root sheath, and outer root sheath which contain predominantly keratinocytes, and FIG. 1D is the dermal sheath containing NBDS cells (also occasionally referred to as the connective-tissue sheath).

The upper dermal sheath (FIG. 1D) can, within certain embodiments, be further separated, for example, by cutting length-wise along one side, or, by using techniques such as enzymatic digestion (e.g., with collagen digesting enzymes such as collagenase, dispase and leupeptin).

The dermal sheath containing NBDS cells, or the separated NBDS cells can then be cultured in a media which promotes cell proliferation. Suitable media include, for example, Williams E, Amniomax, DMEM, Cell Gro MSC medium, FGM-CD, but any other fibroblast or stem cell or hematopoietic cell growth media might be suitable. The media may have added various concentrations of FCS, FCS-substitutes or human autologous or allogenic serum. After 48-72 hours the proliferation medium is typically exchanged for fresh medium (although, within certain embodiments other time-points might be suitable as well). Subsequently the medium can be changed every 2 to 4 days. When the culture has reached approximately 80% (but not limited to) confluence, the cells are detached from the culture flask (typically via trypsinization, although other methods such as scrapping the cells off may also be utilized), and seeded in a larger tissue culture flask. This step is repeated until the desired number of cells is obtained (generally between approximately 10 cells and billions of cells, although more preferably, between millions (e.g., one million and 1 billion) cells.

Cultured cells can be optionally washed several times, and stored in suitable media, or, optionally, frozen in suitable media.

All cell culture supernatants will not be discarded as they contain individual growth factors, matrix molecules, stem cell factors, made by the patients cells. Cell culture supernatants will be frozen, freeze-dried or any other storage method to be suitable for the specific use.

Preparation of Compositions Comprising NBDS Cells

As noted above, NBDS cells may be contained within compositions comprising a variety of ingredients, such as, for example, blood serum or plasma, platelet-rich plasma (PRP), fibrin, (e.g., human albumin), and/or hyaluronic acid. Other commercially available products may also be utilized to prepare suitable compositions, including for example, TISSEEL and COSEAL (available from Baxter), TISSUCOL, BERIPLAST, QUIXIL, TACHOSIL, and EVICEL. Other polymer-based compositions may also be utilized, including for example, polyethylene glycols, poly-lactic acids, and poly caprolactones. Within other embodiments, the cells may be placed in either manufactured or harvested extracellular matrices (e.g., US 2010/0047305 or US 2010/0124573). Within other embodiments, the cells may be placed within a non-biodegradable, or, biodegradable scaffold, or other structure. Particularly preferred scaffolds or structures include biodegradable scaffolds (e.g., collagen-based scaffolds, such as, for example, meshes). Representative examples of suitable scaffolds include, for example, U.S. Pat. Nos., 5,736,372, 5,759,830, 8,039,258 and 8,105,380, all of which are incorporated by reference in their entirety. Within preferred embodiments of the invention, when the composition is to be administered to the synovial fluid of a joint, it is desirable to not include any factors which might create or cause scarring or fibrosis.

Within other preferred embodiments the composition is provided in one or two or more parts (e.g., in a double barrelled syringe that admixes components, or in bi- or multi-chambered cartridges) that is freely flowing and injectable. Representative examples of such syringes include those described in U.S. Pat. Nos. 5,750,657 and 8,039,021, which are both incorporated by reference in their entirety.

Other ingredients may also be included within these compositions, including for example, components of the extracellular matrix (e.g., glycosaminoglycans (GAGs), heparin sulfate, chondroitin sulfate, keratin sulfate, hyaluronic acid, elastin, collagens, fibronectins and laminins), cytokines and chemokines (e.g., transforming growth factor beta (TGF-beta) and its isoforms, insulin-like growth factor (IGF) and its isoforms, granulocyte-macrophage colony-stimulating factor (GM-CSF), parathyroid-hormone-related protein, hepatocyte growth factor/scatter factor (HGF/SF), macrophage stimulating protein (MSP), epidermal growth factor (EGF), interleukin 6 (IL-6), stem cell factor (SCF) stromal cell-derived factor 1 (SDF-1), platelet derived growth factor (PDGF) and fibroblast growth factor (FGF) and/or various therapeutic agents (e.g., analgesic agents, anti-inflammatory agents, antibiotics, antimycotics, antiviral and immunomodulatory agents).

Methods for Treating Joints Utilizing NBDS Cells

Methods are also provided for treating or preventing joint aging or joint injuries, comprising the step of administering to a subject a composition comprising NBDS cells as described above. Typically, cells are administered by injection, although within various embodiments, to the extent a surgical method is employed the cells may be provided directly into the synovial cavity containing the synovial fluid, the articular cartilage, the synovial membrane, joint attached mensisci or ligaments or the articular capsule.

A large number of species may be treated with NBDS cells and compositions provided herein, including for example, mammals such as humans, horses, dogs and cats.

Procedures Utilizing NBDS Cells or Cell Culture Supernatants of Thereof

Within various embodiments, the NBDS cells can be delivered via injections, which can be done with or without local or systemic analgesia or sedation. This can be done with a single or a multi-needle device. In addition, it can be performed either by a single injection as a bolus or multiple, multilayered injections. The delivered volumes/cell numbers largely depend on the indication and the area to be treated. Typical doses may start from as low as 0.01 ml up to several ml. In certain aspects of the invention the injected cell numbers may range from 10 to billions of cells, and more preferably, from 100, 1,000, 10,000, 100,000, 1,000,000 and/or 10,000,000 up to a billion or more cells. The number of injected cells will depend on, among other things, the size of the area to be treated, the total number of cells available and the volume injected, as well as the desired degree of efficacy.

Within yet other aspects of the invention NDBS cell culture supernatants are provided in a suitable preparation. Specifically, cell culture supernatant can be applied into the synovial fluid by itself, or concentrated and admixed with other ingredients suitable for use. Within preferred embodiments the NDBS cell culture supernatant is admixed with hyaluronic acid prior to administration.

Use of Cell Culture Supernatants for Coating Surgical Implants

Single or multi surgical implants are commonly used to treat osteoarthrosis or other cartilage of bone defects. Hence, within one embodiment of the invention medical implants are provided which are coated with, or otherwise adapted to release a cell culture supernatant as described herein. As the cell culture supernatants of NBDS cells contain growth factors and other factors which might be useful to facilitate healing and proper integration of implants. Therefore, the coating of those implants is desirable to reduce fibrous encapsulation and increase biocompatibility of implants or other medical devices.

Within yet other aspects of the invention NDBS cell culture supernatants are provided for the coating of surgical implants to facilitate the ingrowth/healing.

The following examples illustrate the invention and should not be understood as limiting the scope of the invention.

EXAMPLE 1

Tissue Sampling

A skin biopsy from the occipital area of the scalp is obtained from a subject as follows. Briefly, once an appropriate area of the scalp has been selected, it is shaved with hair clippers, ensuring some stubble remains. The biopsy area is then thoroughly disinfected and anaesthetized. Once anesthesia has taken effect, a 4-10 mm deep punch biopsy is gently removed from the biopsy site and the incision closed with sutures which can be removed 12-14 days later. The skin biopsy is then packaged under aseptic conditions into a pre-labelled biopsy tube containing biopsy transport medium, composed of DMEM/Hams F12 with antibiotics.

EXAMPLE 2

Isolation and Cultivation of NBDS Cells

A sterility test is performed on the medium in which the biopsy has been transported to ensure the sample is free from contamination, or alternatively, if the sample is contaminated to ensure that medium with antibiotics is subsequently utilized. The biopsy is then washed several times to remove the biopsy transportation medium and any debris to prepare the tissue for subsequent processing. Hair follicles are processed in Hams F10 by cutting away the skin epithelium with a sterile scalpel and "plucking" or dissecting the whole hair follicle unit from the surrounding dermal tissue using sterile forceps. The hair follicle is gripped with a forceps as close as possible to the skin surface and the follicle exposed by pulling up on the hair in the hair follicle unit. Follicles in the anagen phase (growing phase of the hair cycle, indicated by the visible outer root sheath, and DSC of the hair bulb) are selected for further processing.

NBDS isolation is performed in Hams F10 by first detaching the follicular dermal sheath cup cells and papilla from the rest of the hair follicle using a fine sterile mini-scalpel or needle, and discarded. The dermal sheath containing NBDS cells is removed, and the tissue is prepared for cultivation.

Six to ten dermal sheath tissues are gently placed into 3% hyaluronic acid gel and covered with cell proliferation promoting culture medium such as, for example, DMEM/Hams F12 supplemented with FGF, 10% FCS and antibiotics. After 3 to 5 days, fresh proliferation medium is added to the culture. Subsequently the medium is changed every 2 to 4 days. When the culture has reached approximately 80 to 90% confluence, the cells are detached from the culture flask via trypsinization, and seeded in larger tissue culture flasks. This step is repeated for four passages to obtain approximately 100 million cells.

Once approximately 100 million cells are obtained, the cells are washed with PBS, trypsinized and resuspended in Cell Transportation Medium (CTM: Ringer lactate containing 10% human serum albumin and 5% dimethylsulfoxide). The cells are sedimented by centrifugation and pooled together. The supernatant is aspirated and the cell pellet is resuspended in CTM. Two cell samples/aliquots are removed from the cell-CTM mixture for quality control and cell counting. After the cells are counted, they are sedimented once more by centrifugation, and the resulting pellet is resuspended in CTM to give a final concentration of 20 million cells/ml. The final cell products are stored below −130° C. in liquid nitrogen till shipment.

EXAMPLE 3

Preparation and Administration of NBDS Cells into a Joint

The skin over the joint to be treated is first prepared for injection by application of a topical analgesia (e.g., EMLA-cream) for approximately one hour. Thereafter, the skin is washed and disinfected. NBDS cells, prepared as described above, are then injected into the affected joint as a bolus or in a repetitive manner.

Alternatively, NBDS cells may be injected by arthroscopic guidance directly into the synovial fluid, or damaged cartilage or menisci, or ligaments, or into the bone defects arising from osteoarthrosis in order to fill the entire surface of the desired treatment area.

All of the U.S. patents, U.S. patent application publications, U.S. patent applications, foreign patents, foreign patent applications and non-patent publications referred to in this specification and/or listed in the Application Data Sheet are incorporated herein by reference, in their entirety.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A method for treating a joint, comprising the step of administering into a joint of a subject a composition comprising isolated Non-Bulbar Dermal Sheath (NBDS) cells, where the NBDS cells have been isolated from an outer dermal sheath of a hair follicle, where the outer dermal sheath of the hair follicle is located above the bulbar portion of the hair root but below the base of the sebaceous gland canal.

2. The method according to claim 1 wherein said treatment is due to a joint injury.

3. The method according to claim 2 wherein said joint injury is an acute or chronic osteoarthrosis.

4. The method according to claim 1 wherein said isolated NBDS cells are provided by a method comprising:
   (a) obtaining vital hair from a subject;
   (b) cleaving the hair obtained in step (a) to remove the hair follicle bulb and obtain an isolated dermal sheath;
   (c) isolating Non-Bulbar Dermal Sheath tissue from the dermal sheath product of step (b); and
   (d) cultivating the isolated Non-Bulbar Dermal sheath tissue to produce isolated NBDS cells.

5. The method according to claim 4 wherein said vital hair is obtained by biopsy from a hair on the scalp of a subject.

6. The method according to claim 4 wherein said isolated NBDS cells can either be used autologous or allogenic.

7. The method according to claim 4 wherein said hair is cleaved utilizing a micromanipulator and scalpel, or scissors.

8. The method according to claim 4, further comprising the step of digesting said isolated Non-Bulbar Dermal Sheath tissue by an enzymatic digestion.

9. The method according to claim 8 wherein said enzymatic digestion comprises an enzyme selected from the group consisting of collagenase hyaluronidase, DNAse, elastase, papain, protease type XIV, trypsin, and dispase.

10. The method according to claim 4 wherein said NBDS cells are passaged over multiple passages.

11. The method of claim 1 wherein said composition further comprises serum plasma or platelet-rich plasma (PRP).

12. The method of claim 1 wherein said composition further comprises fibrin and/or hyaluronic acid.

13. The method of claim 1 wherein said composition further comprises at least one of (a) a component of the extracellular matrix, (b) a cytokine, (c) a chemokine or (d) a therapeutic agent.

14. The method of claim 13 wherein said composition comprises one or more components selected from the group consisting of glycosaminoglycans (GAGS), heparin sulfate, chondroitin sulfate, keratin sulfate, hyaluronic acid, elastin, collagens, fibronectins and laminins.

15. The method of claim 13 wherein said composition comprises one or more cytokines selected from the group consisting of transforming growth factor beta (TGF-beta), insulin-like growth factor (IGF), granulocyte-macrophage colony-stimulating factor (GM-CSF), parathyroid-hormone-related protein, hepatocyte growth factor/scatter factor (HGF/SF), macrophage stimulating protein (MSP), epidermal growth factor (EGF), interleukin 6 (IL-6), stromal cell-derived factor 1 (SDF-1), platelet derived growth factor (PDGF) and fibroblast growth factor (FGF).

16. The method of claim 13 wherein said composition comprises one or more therapeutic agents selected from the group consisting of analgesic agent, anti-inflammatory agent, antibiotic, antiviral, antimitotic, and immunomodulatory agent.

17. The method of claim 1 wherein said composition further comprises a scaffold.

18. The method of claim 17 wherein said scaffold is a biodegradable scaffold.

19. The method of claim 1 wherein said composition further comprises NBDS cell culture supernatant.

20. The method of claim 1 wherein said composition does not contain bulbar cells.

* * * * *